United States Patent [19]

Untch et al.

[11] 4,049,697

[45] Sept. 20, 1977

[54] (DL)-13-SUBSTITUTED SULFINYL-PROSTAGLANDIN-LIKE COMPOUNDS AND METHODS OF MAKING

[75] Inventors: Karl G. Untch, Los Altos, Calif.; Gilbert J. Stork, New York, N.Y.

[73] Assignee: Syntex (U.S.A.) Inc., Palo Alto, Calif.

[21] Appl. No.: 673,846

[22] Filed: Apr. 5, 1976

Related U.S. Application Data

[62] Division of Ser. No. 476,362, June 5, 1974, Pat. No. 3,970,685.

[51] Int. Cl.$^2$ ............................................. C07C 177/00
[52] U.S. Cl. .................................... 560/118; 260/399; 260/514 D; 560/121
[58] Field of Search ...................... 260/468 D, 514 D

[56] References Cited

PUBLICATIONS

Tang et al., JACS 92, 2100 (1970).

Primary Examiner—Robert Gerstl
Attorney, Agent, or Firm—Gerard A. Blaufarb; William B. Walker

[57] ABSTRACT (dl)-13-Substituted sulfinyl-prostaglandin-like [(dl)-2α-substituted-3β-(1α-substituted sulfinyl-trans-2-alkenyl)-1-oxygenated cyclopentane and (dl)-2α-substituted-3β-(1α-substituted sulfinyl-trans-2-alkenyl)-4-oxygenated-1-oxygenated cyclopentane] compounds exhibit prostaglandin-like biological properties and are also useful intermediates in the preparation of known prostaglandins.

3 Claims, No Drawings

(DL)-13-SUBSTITUTED SULFINYL-PROSTAGLANDIN-LIKE COMPOUNDS AND METHODS OF MAKING

This is a division of application Ser. No. 476,362, filed June 5, 1974, now U.S. Pat. No. 3,970,085.

SUMMARY OF THE INVENTION

Amongst the novel (dl)-13-substituted sulfinyl-prostaglandin-like [(dl)-2α-substituted-3β-(1α-substituted sulfinyl-trans-2-alkenyl)-1-oxygenated cyclopentane and (dl)-2α-substituted-3β-(1α-substituted sulfinyl-trans-2-alkenyl)-4-oxygenated-1-oxygenated cyclopentane] compounds of our invention are those represented by the formulas:

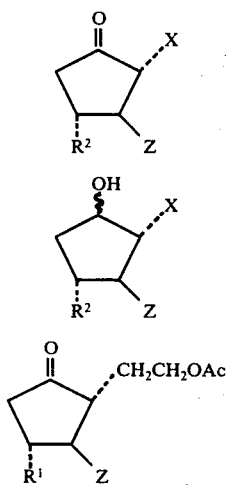

wherein Ac is acetyl;
R$^1$ is hydrogen or OR$^6$, in which R$^6$ is hydrogen, 2-tetrahydropyranyl or dimethyl-t-butylsilyl;
R$^2$ is hydrogen or hydroxyl;

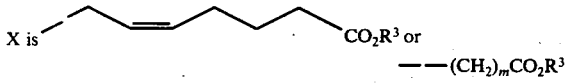

in which
R$^3$ is hydrogen or alkyl containing from one through three carbon atoms, and m is a whole integer from two through eight;

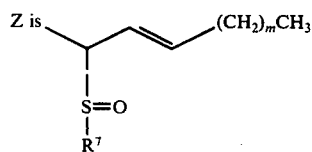

in which R$^7$ is alkyl containing from one through six carbon atoms, cycloalkyl containing from five through seven carbon atoms, chloromethyl, trichloromethyl, trifluoromethyl, chlorodifluoromethyl, dichlorofluoromethyl, β-chloroethyl, α-chloroethyl, α-chloro-β-trichloroethyl, phenyl, p-tolyl, p-chlorophenyl, p-fluorophenyl, 2,4-dichlorophenyl, or 2,5-dichlorophenyl, and m is defined as above; and
the wavy line (ξ) represents the α or β configuration or mixtures thereof; and the non-toxic, pharmaceutically acceptable salts of the compounds of Formulas (A) and (B) when R$^3$ is hydrogen.

BACKGROUND OF THE INVENTION

1. The Invention

This invention relates to (dl)-13-substituted sulfinyl-prostaglandin-like [(dl)-2α-substituted-3β-(1α-substituted sulfinyl-trans-2-alkenyl)-1-oxygenated cyclopentane and (dl)-2α-substituted -3β-(1α-substituted sulfinyl-trans-2-alkenyl)-4-oxygenated-1-oxygenated cyclopentane] compounds.

More particularly, it relates to prostaglandin-like compounds of Formulas (A) through (C) above (whose nomenclature is discussed more fully below).

2. The Prior Art prostaglandins have classically been described as chemically related 20-carbon chain hydroxy fatty acids having the basic skeleton of prostanoic acid:

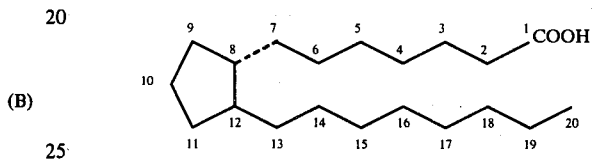

The prostaglandins having an hydroxyl group at the C-11 position and a keto group at the C-9 position are known as the PGE series, those having an hydroxyl group in place of the keto group are known as the PGF series and are further designated by an α or β suffix to indicate the configuration of the hydroxyl group at said position. The natural compounds are the α-hydroxy substituted compounds. They may contain different degrees of unsaturation in the molecule, particularly at C-5, C-13 and C-17, the unsaturation is also indicated by a suffix. Thus, for example, PGE$_1$ refers to a prostanoic acid having a trans olefin bond at the 13-position. For a review on prostaglandins and the definition of primary prostaglandins, see, for example, S. Bergstrom, Recent Progress in Hormone Research 22, pp. 153–175 (1966) and Science 157, page 382 (1967) by the same author.

Frostaglandins are widely distributed in mammalian tissues and have been isolated from natural sources in very small amounts. In addition a number of the natural occurring prostaglandins have been prepared by chemical synthesis; note, for example, J. Am. Chem. Soc. 91, 5675 (1969), J. Am. Chem. Soc. 92, 2586 (1970) and J. Am. Chem. Soc. 93, 1489–1493 (1971) and references cited therein, W. P. Schneider et al., J. Am. Chem. Soc. 90, 5895 (1968). U. Axen et al., Chem. Commun., 303 (1969), and W. P. Schneider, Chem. Commun., 304 (1969).

Because of the remarkable range of biological and pharmacological properties exhibited by this family of compounds, a great deal of interest has focused upon such compounds and accordingly we have discovered novel (dl)-13-sulfinyl-prostaglandin-like [(dl)-2α-substituted-3β-(1α-substituted sulfinyltrans-2-alkenyl)-1-oxygenated cyclopentane and (dl)-2α-substituted-3β-(1α-substituted sulfinyl-trans-2-alkenyl)-4-oxygenated-1-oxygenated cyclopentane] compounds.

FURTHER DESCRIPTION OF THE INVENTION AND PREFERRED EMBODIMENTS

As discussed above prostaglandins have, for the most part, classically been named using as the base for such nomenclature the 20-carbon chain hydroxy fatty acids having the basic skeleton of prostanoic acid. For the naturally occurring prostaglandins this nomenclature has sufficed.

However, in view of the lengthening and shortening of the side chains (and the increased complexity of the side chains) attached at the C-2 and C-3 carbon atoms of the cyclopentane nucleus, as well as other substituents attached to the cyclopentane nucleus, it is readily apparent that a more systematic nomenclature must be used.

Therefore, in the description which follows, the compounds will be named as substituted cyclopentanes in which the cyclopentane nucleus will be numbered as follows:

Thus (dl)-PGE$_1$ having the structure

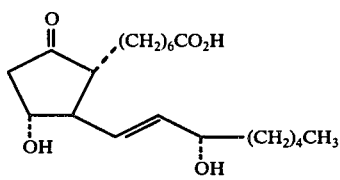

(1)

would be systematically named (dl)-2α-(6-carboxyhexyl)-3β-(3α-hydroxy-trans-1-octenyl)-4α-hydroxy-1-oxocyclopentane.

According to already established convention in the art, the chain attached to the C-3 carbon atom of the cyclopentane ring of naturally occurring prostaglandins having a trans double bond nearest to said C-3 carbon atom is depicted by structural configuration formula thusly

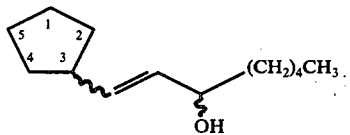

(2)

However, when the chain attached to the C-3 carbon of the cyclopentane ring contains a cis double bond nearest to said C-3 carbon atoms, as in the starting compounds of Formula (I), it is to be understood that the portion of the alkyl side chain attached to the carbon atom adjacent to the double bond is written as shown in Formulas (3) and (4). Hence, the following structural configuration formula

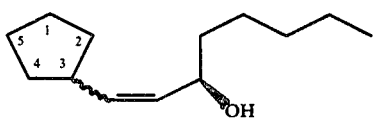

(3)

embodies the above convention for depicting cis prostaglandin-like compounds.

For example. (dl)-2α-(6-carboxyphenyl)-3β-(3β-hydroxy-cis-1-octenyl)-4α-hydroxy-1-oxocyclopentane is depicted by structural configuration formula thusly

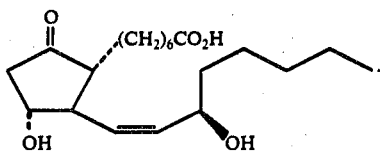

(4)

It is to be understood and will be apparent to those skilled in the art that the compounds of Formulas (A) through (C) above and (I) through (VI) below exist as (dl) pairs. Thus, the (dl) pairs are a mixture of the d and l isomers. For example, the compounds of Formula (II) are actually a mixture of

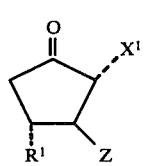

(II)

and its mirror image,

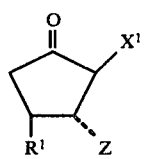

(II$_1$)

Again, to avoid undue prolixity, only one isomer, namely that analogous to that depicted by Formula (II), rather than Formula (II$_1$), will be shown, it being understood that in the specification and claims the mirror images are also encompassed thereby.

It is to be further understood that encompassed within this invention are racemic mixtures and diastereomeric mixtures.

The novel compounds of our invention and novel processes for their production are illustratively represented by the following reaction sequence:

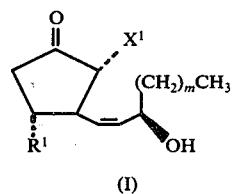

(I)

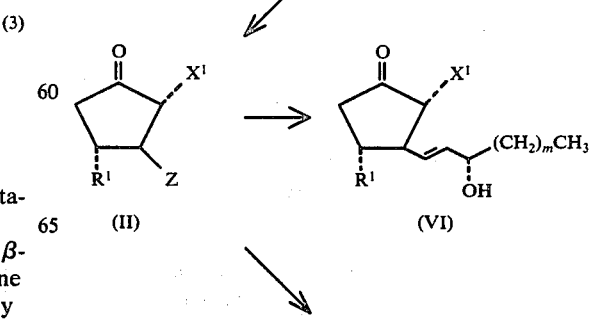

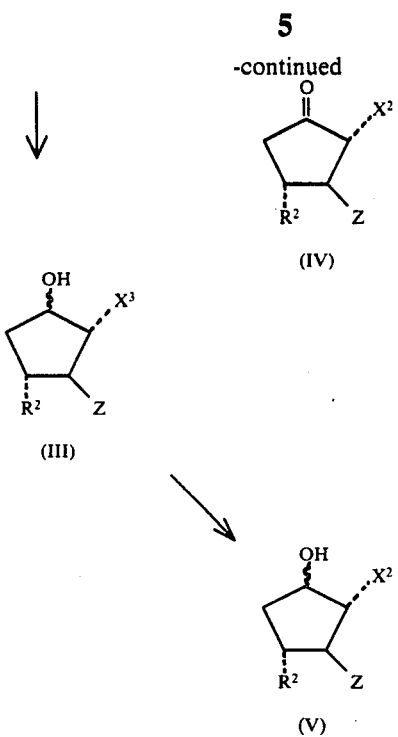

wherein

R¹ is hydrogen or OR⁶, in which R⁶ is hydrogen, 2-tetrahydropyranyl or dimethyl-t-butylsilyl;

R² is hydrogen or hydroxyl;

X¹ is —CH₂CH₂OAc, in which Ac is acetyl,

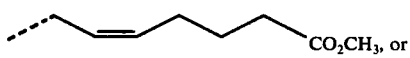

in which m is defined as above;

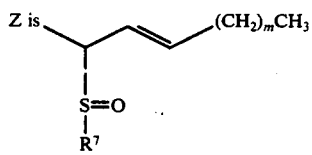

in which R⁷ is alkyl containing from one through six carbon atoms, cycloalkyl containing from five through seven carbon atoms, chloromethyl, trichloromethyl, trifluoromethyl, chlorodifluoromethyl, dichlorofluoromethyl, β-chloroethyl, α-chloroethyl, α-chloro-β-trichloroethyl, phenyl, p-tolyl, p-chlorophenyl, p-fluorophenyl, 2,4-dichlorophenyl, or 2,5-dichlorophenyl; and m is defined as above;

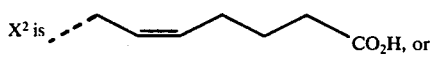

in which m is defined as above;

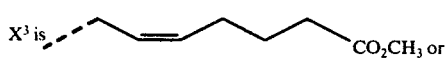

in which m is defined as above; and the wavy line (ξ) represents the α or β configuration or mixtures thereof.

The terms "alkyl containing from one through six carbon atoms" or "alkyl containing from one through three carbon atoms" includes both straight and branched chain alkyl groups; and the broken line ( ) represents the α-configuration.

The reaction steps and definitions given above represent an overall view of the methods used for the preparation of the novel compounds of this invention. For a more detailed explanation of the reaction steps reference can be made to the examples.

In addition, the compounds of Formula (II) are also intermediates since they can be converted to the compounds of Formula (VI) in which the hydroxy group of the chain attached at the C-3 position of the cyclopentane nucleus is in the natural (or α) configuration.

The compounds of Formula (I), and processes for their preparation are disclosed in aband. application Ser. No. 313,461, filed Dec. 8, 1972, copending application Ser. No. 476,360, filed June 5, 1974, and copending application Ser. No. 476,361, filed June 5, 1974, both abandoned, which applications are hereby incorporated by reference and made a part hereof.

In carrying out the processes of our invention, the compounds of Formula (I) are reacted with a substituted sulfenyl chloride of the formula ClSR⁷, wherein R⁷ is defined as above, in the presence of an amine base e.g., triethylamine, N-methyl-pyrrolidine, pyridine, preferably, triethylamine, in an organic solvent, e.g., diethyl ether, tetrahydrofuran, dimethoxyethylene glycol, preferably diethyl ether, at a temperature of from 0° to 35° C., preferably at room temperature (about 20° C.), to obtain the compounds of Formula (II). Suitable substituted sulfenyl chlorides of the formula ClSR⁷ are:

methylsulfenyl chloride,
ethylsulfenyl chloride,
propylsulfenyl chloride,
isopropylsulfenyl chloride,
n-butylsulfenyl chloride,
isobutylsulfenyl chloride,
n-pentylsulfenyl chloride,
isopentylsulfenyl chloride,
n-hexylsulfenyl chloride, and the like,
cyclopentylsulfenyl chloride,
cyclohexylsulfenyl chloride,
cycloheptylsulfenyl chloride,
chloromethylsulfenyl chloride,
trichloromethylsulfenyl chloride,
trifluoromethylsulfenyl chloride,
chlorodifluoromethylsulfenyl chloride,
dichlorofluoromethylsulfenyl chloride,
β-chloroethylsulfenyl chloride,
α-chloroethylsulfenyl chloride,
α-chloro-β-trichloroethylsulfenyl chloride,
benzenesulfenyl chloride,
p-toluenesulfenyl chloride,
p-chlorobenzenesulfenyl chloride,
2,4-dichlorobenzenesulfenyl chloride, and
2,5-dichlorobenzenesulfenyl chloride.

The compounds of Formula (II), wherein R¹ is hydrogen or hydroxyl (and X¹ is defined as above but exclusive of —CH₂CH₂OAc) are treated with a reducing agent to convert them to the compounds of Formula (III), the 1α-and 1β-hydroxy compounds. Suitable reducing agents are sodium borohydride, zinc borohydride, and the like, preferably sodium borohydride, and the reaction is carried out in methanol, ethanol, propanol, and the like, preferably methanol. The temperature for this reaction can vary from −10° to 25° C., however, an initial temperature of 0° C, is preferred. The thus-obtained compounds of Formula (III) are, if desired, separated into the individual 1α-hydroxy and 1β-hydroxy compounds.

The methyl ester compounds of Formula (II), wherein $R^1$ is hydrogen and hydroxyl, and the compounds of Formula (III), are hydrolyzed to obtain the corresponding free acids of Formulas (IV) and (V), respectively. The hydrolysis of the methyl ester is carried out biologically, preferably exzymatically, using a pancreatic lipase preparation to cleave the methyl ester group, thus yielding the free acids. The free acids are separated by column or thin-layer chromatography.

The free acid compounds of Formulas (IV) and (V) can be converted to their corresponding ethyl and propyl esters by treatment with an excess of diazoalkane, e.g., diazoethane or diazopropane in ether or ethyl acetate, or mixtures thereof, in a conventional manner.

As noted above, the free acid compounds of Formulas (A) and (B) [or Formulas (IV) and (V)] can also be administered in the form of their pharmaceutically acceptable salts, i.e., salts which do not significantly adversely affect the pharmaceutical properties of the parent compounds. Suitable pharmaceutically acceptable salts include, for example, the salts of sodium, potassium, aluminum, calcium, iron, magnesium, ammonia, and the like. The salts can be prepared according to conventional procedures and, for example, can be conveniently prepared by treating the corresponding free acids with about one molar equivalent of a pharmaceutically acceptable base per molar equivalent of free acid. Suitable pharmaceutically acceptable bases include, for example, sodium bicarbonate, potassium bicarbonate, ammonium hydroxide, trimethylamine, triethylamine, tripropylamine, β-(dimethylamino)ethanol, β-(diethylamino)ethanol, arginine, lysine, caffeine, procaine and the like. Typically the reaction is conducted in an aqueous solution, alone or in combination with an inert, water miscible organic solvent, at a temperature of about from 0° to 30° C., preferably at room temperature. Typical inert water miscible organic solvents include methanol, ethanol, isopropanol, butanol, dioxane, tetrahydrofuran and the like. The salts can also be prepared via conventional ion exchange procedures.

The compounds of Formulas (A) and (B) exhibit prostaglandin-like biological activities and thus are useful in the treatment of mammals where the use of prostaglandins is indicated. The compounds (and pharmaceutically acceptable salts) are bronchodilators and thus are useful in treating mammals for bronchial spasm or wherever strong bronchodilators are indicated. The compounds are also useful in controlling or palliating hypertension in mammals and further exhibit central nervous system depressant activity, in mammals, and are useful as sedatives. In addition, the compounds are useful for inducing labor, in pregnancy, and for inducing menses to correct or reduce menstrual abnormalities. The compounds also possess anti-fertility properties. In addition, they exhibit anti-inflammatory activities and thus are useful as anti-inflammatory agents. The compounds of Formulas (A) and (B) can be administered in a wide variety of dosage forms, either alone or in combination with other pharmaceutically compatible medicaments, in the form of pharmaceutical compositions suited for oral or parenteral administration or inhalation in the case of bronchodilators. The compounds are typically administered as pharmaceutical compositions consisting essentially of the compounds and/or salts, of the invention, and a pharmaceutical carrier. The pharmaceutical carrier can be either a solid material, liquid, or aerosol, in which the compound and/or salt is dissolved, dispersed or suspended, and can optionally contain small amounts of preservatives and/or pH-buffering agents. Suitable preservatives which can be used include, for example, benzyl alcohol and the like. Suitable buffering agents include, for example, sodium acetate and pharmaceutical phosphate salts and the like.

The liquid compositions can, for example, be in the form of solutions, emulsions, suspensions, syrups, or elixirs. The solid compositions can take the form of tablets, powders capsules, pills or the like, preferably in unit dosage forms for simple administration or precise dosages. Suitable solid carriers include, for example, pharmaceutical grades of starch, lactose, sodium saccharin talcum, sodium bisulfite and the like.

For inhalation administration, the compounds can, for example, be administered as an aerosol comprising the compounds or salts in an inert propellant together with cosolvent (e.g., ethanol) together with optional preservatives and buffering agents. Additional general information concerning the inhalation administration of aerosols can be had by reference to U.S. Pat. Nos. 2,969,691 and 3,095,355.

The compounds of Formulas (A) and (B) are typically administered in dosages of about from 0.01 to 10 mg. per kg. of body weight. The precise effective dosage will, of course, vary depending upon the mode of administration, condition being treated, and host.

The compounds of Formula (II) can be converted to the compounds of Formula (VI) in which the hydroxy group of the chain attached at the C-3 position of the cyclopentane nucleus is in the natural (or α) configuration. This conversion is carried out by treating the compounds of Formula (II) with a sulfenate cleaving agent. Suitable sulfenate cleaving agents are thiophilic reagents, e.g., trivalent phosphorous compounds, such as trialkylphosphites and trialkylphosphines in which each alkyl group is the same and contains from one to four carbon atoms, preferably trimethylphosphite; nucleophilic sulfur reagents such as thiophenolate anion; and secondary amines such as piperidine, pyrrolidine, and the like, in the presence of an organic solvent, e.g., methanol, ethanol, ethyl acetate, chloroform, preferably methanol, at a temperature of 0° to 50° C., preferably room temperature (about 20° C.), while monitoring the reaction by thin-layer chromatography. The compounds of Formula (VI) wherein $R^1$ is $OR^6$, in which $R^6$ is 2-tetrahydropyranyl or dimethyl-t-butylsilyl, can be deetherified, according to methods known in the art, to obtain the compounds of Formula (VI) wherein $R^1$ is $OR^6$, in which $R^6$ is hydrogen [which are the corresponding 4α-hydroxy compounds of Formula (VI)].

It is to be understood that any of the compounds obtained can be separated and/or purified by any suitable separation and/or purification procedure, such as, for example, extraction, filtration, distillation, evaporation, crystallization, column chromatography, thin-layer chromatography, and the like. Specific illustrations of typical separation and/or purification procedures can be had by reference to the preparation and examples described herein below. However, other equivalent separation and/or purification procedures could, of course, also be used.

A further understanding of the invention can be had from the following non-limiting preparation and examples. Also, where necessary, the preparation and examples are repeated to provide starting materials for subsequent examples.

PREPARATION 1

This preparation illustrates methods of preparing a pancreatic lipase preparation which can be used to convert the carbomethoxy cyclopentanes to carboxy cyclopentanes. In this preparation, 10 g. of crude pancreatic lipase [note: Biochem. Biophysics Acta., v. 23, p. 264 (1957)] is suspended in 65 ml. of water at 0° C. The suspension is stirred for one hour at 0° C. and then centrifuged for 20 minutes at 10,000 × g. The supernatant liquid is separated and maintained at 0° C. for later use. The precipitate is again suspended in 65 ml. of water at 0° C. and centrifuged as before. The supernatant liquid is separated and combined with the previously obtained supernatant liquid and then added to 130 ml. of saturated aqueous ammonium sulfate solution at 0° C., with stirring, and then allowed to stand for five minutes. The resulting mixture is then centrifuged at 10,000 × g. for 20 minutes. The supernatant liquid is decanted and the precipitate is collected, then dissolved in sufficient water to yield 125 ml. of solution. 15 Ml. of saturated aqueous ammonium sulfate solution is then added to the water solution yielding a suspension which is then centrifuged at 10,000 × g. for 20 minutes. The supernatant liquid is collected and treated with 100 ml. of saturated ammonium sulfate affording a second suspension, which is divided into two equal portions. Each portion is again centrifuged for 20 minutes at 10,000 × g., and in each instance the supernatant liquid is discarded (decantation) and the precipitate collected. Each precipitate is stored at 4° C. prior to use.

The pancreatic lipase ester cleaving preparation is then prepared immediately prior to use by dissolving one of the above precipitates in 25 ml. of an aqueous 0.1M sodium chloride solution and 0.05M calcium chloride solution and then adjusting the pH to 7.0 by the careful addition (i.e. titration) of a 0.1M aqueous sodium hydroxide solution.

EXAMPLE 1

To a solution of 125 mg. (0.35 mmole) of (dl)-2α-(6-carbomethoxyhexyl)-3β-(3β-hydroxy-cis-1-octenyl)-1-oxocyclopentane (I) dissolved in 10 ml. of dry diethyl ether containing 106 mg. (1.05 mmole) of triethylamine there is added 80 mg. (0.49 mmole) of freshly distilled p-toluenesulfenyl chloride. The reaction mixture is stirred at room temperature until the yellow color disappears (about twenty minutes) and monitored by thin-layer chromatography. After completion of the reaction, as measured by thin-layer chromatography, the precipitate formed is filtered, and the filtrate thus-obtained is concentrated and purified by preparative thin-layer chromatography (eluting with ethyl acetate::hexane::2:3) to yield (dl)-2α-(6-carbomethoxyhexyl)-3β-(1α-p-tolylsulfinyl-trans-2-octenyl)-1-oxocyclopentane (II), which is further purified by column chromatography (using acetate:hexane) or crystallization from ether-hexane.

Similarly, substituting a stoichiometric equivalent amount of other starting materials of Formula (I) for (dl)-2α-(6-carbomethoxyhexyl)-3β-(3β-hydroxy-cis-1-octenyl)-1-oxocyclopentane, for example, (dl)-2α-(6-carbomethoxy-cis-2-hexenyl)-3β-(3β-hydroxy-cis-1-octenyl)-1-oxocyclopentane, (dl)-2α-(2-acetoxyethyl)-3β-(3β-hydroxy-cis-1-octenyl)-1-oxocyclopentane, (dl)-2α-(6-carbomethoxyhexyl)-3β-(3β-hydroxy-cis-1-octenyl)-4α-hydroxy-1-oxocyclopentane, (dl)-2α-(6-carbomethoxy-cis-2-hexenyl)-3β-(3β-hydroxy-cis-1-octenyl)-4α-hydroxy-1-oxocyclopentane, (dl)-2α-(2-acetoxyethyl)-3β-(3β-hydroxy-cis-1-octenyl)-4α-hydroxy-1-oxocyclopentane, (dl)-2α-(6-carbomethoxyhexyl)-3β-(3β-hydroxy-cis-1-octenyl)-4α-(2-tetrahydropyranyloxy)-1-oxocyclopentane, (dl)-2α-(6-carbomethoxy-cis-2-hexenyl)-3β-(3β-hydroxy-cis-1-octenyl)-4α-(2-tetrahydropyranyloxy)-1-oxocyclopentane, (dl)-2α-(2-acetoxyethyl)-3β-(3β-hydroxy-cis-1-octenyl)-4α-(2-tetrahydropyranyloxy)-1-oxocyclopentane, (dl)-2α-(6-carbomethoxyhexyl)-3β-(3β-hydroxy-cis-1-octenyl)-4β-dimethyl-t-butylsilyloxy-1-oxocyclopentane, (dl)-2α-(6-carbomethoxy-cis-2-hexenyl)-3β-(3β-hydroxy-cis-1-octenyl)-4α-dimethyl-t-butylsilyloxy-1-oxocyclopentane, and (dl-2α-(2-acetoxyethyl)-3β-(3β-hydroxy-cis-1-octenyl)-4α-dimethyl-t-butylsilyloxy-1-oxocyclopentane, is productive of (dl)-2α-(6-carbomethoxy-cis-2-hexenyl)-3β-(1α-p-tolylsulfonyl-trans-2-octenyl)-1-oxocyclopentane, (dl)-2α-(2-acetoxyethyl-3β-(1α-p-tolylsulfinyl-trans-2-octenyl)-1-oxocyclopentane, (dl)-2α-(6-carbomethoxyhexyl)-3β-(1α-p-tolylsulfinyl-trans-2-octenyl)-4α-hydroxyl-1-oxocyclopentane, (dl)-2α-(6-carbomethoxy-cis-2-hexenyl)-3β-(1α-p-tolylsulfinyl-trans-2-octenyl)-4α-hydroxy-1-oxocyclopentane, (dl)-2α-(2-acetoxyethyl)-3β-(1α-p-tolylsulfinyl-trans-2-octenyl)-4α-hydroxy-1-oxocyclopentane, (dl)-2α-(6-carbomethoxyhexyl)-3β-(1α-p-tolylsulfinyl-trans-2-octenyl)-4α-(2-tetrahydropyranyloxy)-1-oxocyclopentane, (dl)-2α-(6-carbomethoxy-cis-2-hexenyl)-3β-(1α-p-tolylsulfinyl-trans-2-octenyl)-4α-(2-tetrahydropyranyloxy)-1-oxocyclopentane, (dl)-2α-(2-acetoxyethyl)-3β-(1α-p-tolylsulfinyl-trans-2-octenyl)-4α-(2-tetrahydropyranyloxy)-1-oxocyclopentane, (dl)-2α-(6-carbomethoxyhexyl)-3β-(1α-p-tolylsulfinyl-trans-2-octenyl)-4α-dimethyl-t-butylsilyloxy-1-oxocyclopentane, (dl)-2α-(6-carbomethoxy-cis-2-hexenyl)-3β-(1α-tolylsulfinyl-trans-2-octenyl)-4α-dimethyl-t-butylsilyloxy-1-oxocyclopentane, and (dl)-2α-(2-acetoxyethyl)-3β-(1α-p-tolylsulfinyl-trans-2-octenyl)-4α-dimethyl-t-butylsilyloxy-1-oxocyclopentane, respectively.

In like manner, other compounds of Formula (I) can be used to obtain the 3β-(1α-p-tolylsulfinyl-trans-2-octenyl]derivatives corresponding thereto.

Likewise, other substituted sulfenyl chlorides substituted for p-toluenesulfonyl chloride, and using the compounds of Formula (I) is productive of the other various 3β-(1α-substituted sulfinyl-trans-2-alkenyl) compounds of Formula (II).

EXAMPLE 2

240 Mg. of (dl)-2α-(6-carbomethoxyhexyl)-3β-(1α-p-tolysulfinyl-trans-2-octenyl)-1-oxocyclopentane (II) is dissolved in 10 ml. of methanol and then cooled to about 0° C. in an ice bath. 5 Ml. of methanol containing 14.0 mg. of sodium borohydride solution are added dropwise until nearly all of the starting material is consumed as determined by thin-layer chromatography. 10 Ml. of 0.1N methanolic hydrochloric acid are added and the reaction mixture is evaporated (in vacuo). 25 Ml. of ethyl acetate and 25 ml. of water are added, the organic layer separated, washed with saturated sodium chloride and dried over anhydrous sodium sulfate according a mixture of (dl)-2α-(6-carbomethoxyhexyl)-3β-(1α-p-tolylsulfinyl-trans-2-octenyl)-1α-and 1β-hydroxycyclopentanes(III).

Similarly, substituting a stoichiometric equivalent amount of other methyl ester compounds of Formula (II), wherein $R^2$ is hydrogen or hydroxyl, for (dl)-2α-(6-carbomethoxyhexyl)-3β-(1α-p-tolylsulfinyl-trans-2-octenyl)-1-oxocyclopentane, for example, (dl)-2α-(6-carbomethoxy-cis-2-hexenyl)-3β-(1α-p-tolylsulfinyl-trans-2-octenyl)-1-oxocyclopentane, (dl)-2α-Z(2-acetoxyethyl)-3β-(1α-p-tolylsulfinyl-trans-2-octenyl)-1-oxocyclopentane, (dl)-2α-(6-carbomethoxyhexyl)-3β-(1α-p-tolylsulfinyl-trans-2-octenyl)-4α-hydroxy-1-oxocyclopentane, (dl)-2α-(6-carbomethoxy-cis-2-hexenyl)-3β-(1α-p-tolylsulfinyl-trans-2-octenyl)-4α-hydroxy-1-oxocyclopentane, and (dl)-2α-(2-acetoxyethyl)-3β-(1α-p-tolylsulfinyl-trans-2-octenyl)-4α-hydroxy-1-oxocyclopentane, is productive of (dl)-2α-(6-carbomethoxy-bis-2-hexenyl)-3β-(1α-p-tolylsulfinyl-trans-2-octenyl)-1α- and 1β-hydroxycyclopentanes, (dl)-2α-(2-acetoxyethyl)-3β-(1α-p-tolylsulfinyl-trans-2-octenyl)-1α- and 1β-hydroxycyclopentanes, (dl-2α-(6-carbomethoxyhexyl)-3β-(1α-p-tolylsulfinyl-trans-2-octenyl)-4α-hydroxy-1α- and 1β-hydroxycyclopentanes, (dl)-2α-(6-carbomethoxy-cis-2-hexenyl)-3β-(1α-p-tolylsulfinyl-trans-2-octenyl)-4α-hydroxy-1α- and 1β-hydroxycyclopentanes, and (dl)-2α-(2-acetoxyethyl)-3β-(1α-p-tolylsulfinyl-trans-2-octenyl)-4α-hydroxy-1α- and 1β-hydroxycyclopentanes, respectively.

In like manner, other 3β-(1α-p-tolylsulfinyl-trans-2-octenyl) methyl ester compounds of Formula (II) are converted to the corresponding 1α- and 1β-hydroxy compounds.

Likewise, other of the 3β-(1α-substituted sulfinyl-trans-2-alkenyl) methyl ester compounds of Formula (II) are converted to the corresponding 3β-(1α-substituted sulfinyl-trans-2-alkenyl)-1α-and 1β-hydroxy compounds of Formula (III).

The 1α- and 1β-hydroxy compounds prepared above can, if desired, be separated into the respective individual 1α-hydroxy and 1β-hydroxy compounds by thin-layer of column chromatography using silica gel with acetone-hexane::3:7 for development and elution. Determination of the configuration of the 1-hydroxy group is made by direct comparison of the $^{13}$C-nmr spectra of the 1-hydroxy isomers. That isomer exhibiting a C-1 resonance at a chemical shift downfield relative to the C-1 resonance of the other isomer is the 1α-hydroxy compound and the other is the 1β-hydroxy compound.

EXAMPLE 3

100 Mg. of (dl)-2α-(6-carbomethoxyhexyl)-3β-(1α-p-tolylsulfinyl-trans-2-octenyl)-1-oxocyclopentane (II) is admixed with 20 ml. of a pancreatic lipase preparation, prepared according to Preparation 1, at room temperature. The mixture is emulsified by sonication for five minutes and then stirred at room temperature for thirty minutes. The mixture is poured into 125 ml. of acetone, filtered and evaporated, under vacuum, and the resulting residue is extracted with four 25 ml. portions of ethyl acetate. The extracts are combined and concentrated by vacuum evaporation. The concentrate is chromatographed on silica gel thin-layer plates using a 9:1 (volume proportion) of chloroform:methanol. The product is removed from the silica gel with 3:1 (volume proportion) of ethyl acetate:methanol. Following filtration and vacuum evaporation of the solvent there is obtained (dl)-2α-(6-carboxyhexyl)-3β-(1α-p-tolylsulfinyl-trans-2-octenyl9-1-oxocyclopentane (IV).

Similarly, substituting a stoichiometric equivalent amount of other 3β-(1α-p-tolylsulfinyl-trans-2-octenyl) and other 3β-(1α-substituted sulfinyl-trans-2-octenyl) methyl ester compounds of Formula (II), wherein $R^1$ is hydrogen or hydroxyl, or Formula (III), either as a mixture of the 1α- and 1β-hydroxy compounds, or as individual 1α-hydroxy and 1β-hydroxy compounds, for (dl)-2α-(6-carbomethoxyhexyl)-3β-(1α-p-tolylsulfinyl-trans-2-octenyl)--oxocyclopentane, for example, (dl)-2α-(6-carbomethoxy-cis-2-hexenyl)-3β-(1α-p-tolylsulfinyl-trans-2-octenyl)-1-oxocyclopentane, (dl)-2α-(6-carbomethoxyhexyl)-3β-(1α-p-tolylsulfinyl-trans-2-octenyl)-4α-hydroxy-1-oxocyclopentane, (dl)-2α-(6-carbomethoxy-cis-2-hexenyl)-3β-(1α-p-tolylsulfinyl-trans-2-octenyl)-4α-hydroxy-1-oxocyclopentane, (dl)-2α-(6-carbomethoxyhexyl)-3β-(1α-p-tolylsulfinyl-trans-2-octenyl)-1α- and 1β-hydroxycyclopentanes, (dl)-2α-(6-carbomethoxy-cis-2-hexenyl)-3β-(1α-p-tolylsulfinyl-trans-2-octenyl)-1α- and 1β-hydroxycyclopentanes, (dl)-2α-(6-carbomethoxyhexyl)-3β-(1α-p-tolylsulfinyl-trans-2-octenyl)-4α-hydroxy-1α- and 1β-hydroxycyclopentanes, and (dl)-2α-(6-carbomethoxy-cis-2-hexenyl)-3β-(1α-p-tolylsulfinyl-trans-2-octenyl)-4α-hydroxy-1αand 1β-hydroxycyclopentanes, is productive of (dl)-2α-(6-carboxy-cis-2-hexenyl)-3β-(1α-p-tolylsulfinyl-trans-2-octenyl)-1-oxocyclopentane, (dl)-2α-(6-carboxyhexyl)-3β-(1α-p-tolylsulfinyl-trans-2-octenyl)-4α-hydroxy-1-oxocyclopentane, (dl)-2α-(6-carboxy-cis-2-hexenyl)-3β-(1α-p-tolylsulfinyl-trans-2-octenyl)-4α-hydroxy-1-oxocyclopentane, (dl)-2α-(6-carboxyhexyl)-3β-(1α-p-tolylsulfinyl-trans-2-octenyl)-1αand 1β-hydroxycyclopentanes, (dl)-2α-(6-carboxy-cis-2-hexenyl)-3β-(1α-p-tolylsulfinyl-trans-2-octenyl)-1α- and 1β-hydroxycyclopentanes, (dl)-2α-(6-carboxyhexyl)-3β-(1α-p-tolylsulfinyl-trans-2-octenyl)-4α-hydroxy-1α- and 1β-hydroxycyclopentanes, and (dl)-2α-(6-carboxy-cis-2-hexenyl)-3β-(1α-p-tolylsulfinyl-trans-2-octenyl)-4α-hydroxy-1α- and 1β-hydroxycyclopentanes, respectively.

Likewise, other of the variously substituted methyl ester compounds of Formula II, wherein $R^1$ is hydrogen or hydroxyl, or Formula (III) can be hydrolyzed to the corresponding free acids.

When the above reaction is carried out on a mixture of 1α-and 1β-hydroxy methyl ester compounds, the individual 1α-hydroxy free acid and 1β-hydroxy free acid compounds can be separated by following the separation procedures described in Example 2 for the obtention of the individual 1α-hydroxy methyl ester and 1β-hydroxy methyl ester compounds and using a 9:1:: chloroform: methanol or 75:25:2::benzene:tetrahydrofuran:formic acid.

EXAMPLE 4

To a solution of 100 mg. of (dl)-2α-(6-carboxyhexyl)-3β-(1α-p-tolylsulfinyl-trans-2-octenyl)-1-oxocyclopentane in 10 ml. of ether/ethyl acetate (1:1 volume) is added an excess of ethereal diazoethane, and the reaction mixture is kept at room temperature for 30 minutes. It is then evaporated to dryness under vacuum, to yield (dl)-2α-(6-carboethoxyhexyl)-3β-(1α-p-tolylsulfinyl-trans-2-octenyl)-1-oxocyclopentane.

By the same method but using diazopropane in place of diazoethane there is produced (dl)-2α-(6-carbopropoxyhexyl)-3β-(1α-p-tolylsulfinyl-trans-2-octenyl)-1-oxocyclopentane.

In a similar manner, the other free acids obtained in Example 3 are converted to the corresponding ethyl or propyl esters.

EXAMPLE 5

This examples illustrates methods of preparing the salts of the invention. 2.0 Ml. of 0.1N aqueous sodium bicarbonate is added to a solution containing 92 mg. of (dl)-2α-(6-carboxyhexyl)-3β-(1α-p-tolylsulfinyl-trans-2-octenyl)-1-oxocyclopentane, in 10 ml. of methanol and the resulting mixture stirred at room temperature for one hour. The mixture is then evaporated to dryness under reduced pressure yielding the sodium salt of (dl)-2α-(6-carboxyhexyl)-3β-(1α-p-tolylsulfinyl-trans-2-octenyl)-1-oxocyclopentane.

Similarly, by following the same procedure but using a stoichiometric amount of potassium bicarbonate (in the form of an aqueous 0.1N solution) in place of sodium bicarbonate, the potassium salt of (dl)-2α-(6-carboxyhexyl)-3β-(1α-p-tolylsulfinyl-trans-2-octenyl)-1-oxocyclopentane is prepared.

Likewise, following the same procedure, the corresponding sodium and potassium salts of the free acids, obtained in Example 3, are respectively prepared.

EXAMPLE 6

74 Mg. (0.155 mmole) of (dl)-2α-(6-carbomethoxyhexyl)-3β-(1α-p-tolylsulfinyl-trans-2-octenyl)-1-oxocyclopentane (II), dissolved in 4 Ml. of absolute methanol, are treated with 109 mg. (1.55 mmole) of trimethylphosphite for 1-2 hours at room temperature. The reaction is monitored by thin-layer chromatography (using ethyl acetate:hexane::1:1) and when complete the reaction mixture is concentrated and purified by preparative thin-layer chromatography (using ethyl acetate:hexane::1:1) to yield (dl)-2α-(6-carbomethoxyhexyl)-3β-(3α-hydroxy-trans-1-octenyl)-1-oxocyclopentane (VI).

Similarly, substituting a stoichiometric equivalent amount of other variously substituted compounds of Formula (II) for (dl)-2α-(6-carbomethoxyhexyl)-3β-(1α-p-tolylsulfinyl-trans-2-octenyl)-1-oxocyclopentane, for example, (dl)-2α-(6-carbomethoxy-cis-2-hexenyl)-3β-(1α-p-tolylsulfinyl-trans-2-octenyl)-1-oxocyclopentane, (dl)-2α-(2-acetoxyethyl)-3β-(1α-p-tolylsulfinyl-trans-2-octenyl)-1-oxocyclopentane, (dl)-2α(6-carbomethoxyhexyl)-3β-(1α-p-tolylsulfinyl-trans-2-octenyl)-4α-hydroxy-1-oxocyclopentane, (dl)-2α-(6-carbomethoxy-cis-2-hexenyl)-3β-(1α-p-tolylsulfinyl-trans-2-octenyl)-4α-hydroxy-1-oxocyclopentane, (dl)-2α-(2-acetoxyethyl)-3β-(1α-p-tolylsulfinyl-trans-2-octenyl)-4α-hydroxy-1-oxocyclopentane, (dl)-2α-(6-carbomethoxyhexyl)-3β-(1α-p-tolylsulfinyl-trans-2-octenyl)-4α-(2-tetrahydropyranyloxy)-1-oxocyclopentane, (dl)-2α-(6-carbomethoxy-cis-2-hexenyl)-3β-(1α-p-tolylsulfinyl-trans-2-octenyl)-4α-(2-tetrahydropyranyloxy)-1-oxocyclopentane, (dl)-2α-(2-acetoxyethyl)-3β-(1α-p-tolylsulfinyl-trans-2-octenyl)-4α-(2-tetrahydropyranyloxy)-1-oxocyclopentane, (dl)-2α-(6-carbomethoxyhexyl)-3β-(1α-p-tolylsulfinyl-trans-2-octenyl)-4α-dimethyl-t-butylsilyloxy-1-oxocyclopentane, (dl)-2α-(6-carbomethoxy-cis-2-hexenyl)-3β-(1α-p-tolylsulfinyl-trans-2-octenyl)-4α-dimethyl-t-butylsilyloxy-1-oxocyclopentane, and (dl)-2α-(2-acetoxyethyl)-3β-(1α-p-tolylsulfinyl-trans-2-octenyl)-4α-dimethyl-t-butylsilyloxy-1-oxocyclopentane, is productive of (dl)-2α-(6-carbomethoxy-cis-2-hexenyl)-3β-(3α-hydroxy-trans-1-octenyl)-1-oxocyclopentane, (dl)-2α-(2-acetoxyethyl)-3β-(3α-hydroxy-trans-1-octenyl)-1-oxocyclopentane, (dl)-2α-(6-carbomethoxyhexyl)-3β-(3α-hydroxy-trans-1-octenyl)-4α-hydroxy-1-oxocyclopentane, (dl)-2α-(6-carbomethoxy-cis-2-hexenyl)-3β-(3α-hydroxy-trans-1-octenyl)-4α-hydroxy-1-oxocyclopentane, (dl)-2α-(2-acetoxyethyl)-3β-(3α-hydroxy-trans-1-octenyl)-4α-hydroxy-1-oxocyclopentane, (dl)-2α-(6-carbomethoxyhexyl)-3β-(3α-hydroxy-trans-1-octenyl)-4α-(2-tetrahydropyranyloxy)-1-oxocyclopentane, (dl)-2α-(6-carbomethoxy-cis-2-hexenyl)-3β-(3α-hydroxy-trans-1-octenyl)-4α-(2-tetrahydropyranyloxy)-1-oxocyclopentane, (dl)-2α-(2-acetoxyethyl)-3β-(3α-hydroxy-trans-1-octenyl)-4α-(2-tetrahydropyranyloxy)-1-oxocyclopentane, (dl)-2α-(6-carbomethoxyhexyl)-3β-(3α-hydroxy-trans-1-octenyl)-4α-dimethyl-t-butylsilyloxy-1-oxocyclopentane, (dl)-2α-(6-carbomethoxy-cis-2-hexenyl)-3β-(3α-hydroxy-trans-1-octenyl)-4α-dimethyl-t-butylsilyloxy-1-oxocyclopentane, and (dl)-2α-(2-acetoxyethyl)-3β-(3α-hydroxy-trans-1-octenyl)-4α-dimethyl-t-butylsilyloxy-1-oxocyclopentane, respectively.

Likewise, other 3β-(1α-substituted sulfinyl-trans-2-alkenyl) compounds of Formula (II) are converted to the 3β-(3α-hydroxy-trans-1-alkenyl)compounds of Formula (VI).

Obviously many modifications of the invention described herein above and below in claims can be made without departing from the essence and scope thereof.

What is claimed is:

1. The (dl) compounds of the formulas:

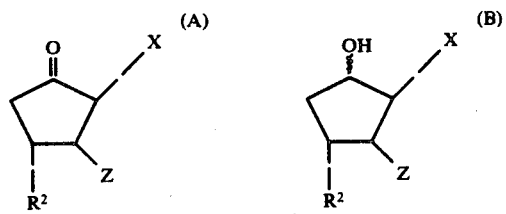

wherein

R² is hydrogen or hydroxyl;

X is ![structure] CO₂R³ or —(CH₂)ₘCO₂R³, in which

R³ is hydrogen or alkyl containing from one through three carbon atoms, and $m$ is a whole integer from two through eight;

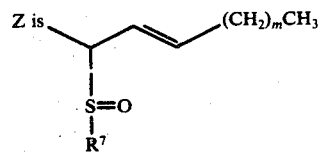

wherein R⁷ is alkyl containing from one through six carbon atoms, cycloalkyl containing from five through seven carbon atoms, chloromethyl, trichloromethyl, trifluoromethyl, chlorodifluoromethyl, dichlorofluoromethyl, β-chloroethyl, α-chloroethyl, or α-chloro-β-trichloroethyl, and $m$ is defined as above; and the wavy line (ξ) represents the α or β configuration or mixtures thereof; and the non-toxic, pharmaceutically acceptable salts of the compounds of Formulas (A) and (B) when R³ is hydrogen.

2. The (dl) compounds of Formula (A) of claim 1.
3. The (dl) compounds of Formula (B) of claim 1.

* * * * *